United States Patent [19]

Jensen et al.

[11] Patent Number: 4,873,193
[45] Date of Patent: Oct. 10, 1989

[54] METHOD AND APPARATUS FOR THE COLLECTION AND PRESERVATION OF FLUID BIOLOGICAL EVIDENCE

[75] Inventors: Richard E. Jensen, St. Peter; Donald H. Nichols, Roseville; D. Gary Hemphill, Wayzata, all of Minn.

[73] Assignee: Forensic Applications Corporation, Minneapolis, Minn.

[21] Appl. No.: 89,586

[22] Filed: Aug. 26, 1987

[51] Int. Cl.⁴ .................... G01N 1/00; B65D 21/00
[52] U.S. Cl. .................... 436/176; 422/102; 206/499; 206/514; 206/516; 206/807; 215/10
[58] Field of Search ............... 220/406, 23.83; 206/499, 514–517, 828, 807; 215/10, DIG. 3; 422/102; 436/176

[56] References Cited

U.S. PATENT DOCUMENTS 3,849,256 11/1974 Linder .................... 422/102
3,883,745 5/1975 Glasser .................... 422/102
4,094,641 6/1978 Friswell .................... 422/102
4,418,702 12/1983 Brown et al. .................... 422/102

Primary Examiner—Barry S. Richman
Assistant Examiner—T. J. Wallen
Attorney, Agent, or Firm—Moore & Hansen

[57] ABSTRACT

An apparatus for collecting and preserving fluid biological evidence comprising a specimen vial and lid, the lid having an adhesive coated disk inserted therein with the lid initially being inverted on the rim of the specimen vial and encased in a tamper evident plastic wrapper. The specimen vial and lid, encased in the tamper evident wrapper, are sealed along with a pair of adhesive backed sealing tapes, an instruction manual, and a compressible foam cushioning pad, within an outer container with a second tamper evident plastic wrapper.

20 Claims, 1 Drawing Sheet

METHOD AND APPARATUS FOR THE COLLECTION AND PRESERVATION OF FLUID BIOLOGICAL EVIDENCE

BACKGROUND OF THE INVENTION

This invention relates generally to devices for collecting and preserving specimens of biological fluid for use as evidence, and particularly to an apparatus and method of using that apparatus for collecting urine specimens and supplying those specimens to a remote laboratory facility for analytical testing.

In recent years, several factors have brought the procedures and practices used for collecting and preserving biological samples into closer inspection. The increase in efforts to inform the public concerning the many dangers of addictive and perception altering drugs, and to stop their widespread usage, is one major force which has fostered this awareness.

Expensive promotional campaigns on television and other media regarding such problems as cocaine and driving while intoxicated have increased public awareness of the personal and public dangers of such drugs, and heightened the public's intolerance to the use of such chemicals when the harm or danger is not merely to the user, but to the public as well.

Increased liability by private companies and public carriers for the negligence and recklessness of its employees, and the opening of widespread drug testing of federal employees, have paved the way towards significantly increased drug testing programs for private sector employees.

Urinalysis has been selected as one preferred vehicle for chemical testing, since it may be performed under the direction and supervision of personnel having no medical training, entails the least intrusion to the body of the person being tested, and the process of sample collection may be performed quickly and inexpensively in the workplace.

Urinalysis has also become an important factor in testing for drivers who are or may be under the influence of a drug or intoxicating liquor. While blood testing is generally considered the most accurate and convincing evidence by the courts, some states permit or require that persons be given the choice between blood and urine testing, on the basis of minimizing the invasion to the persons or their privacy.

The results of employee drug testing programs can often be catastrophic for an individual's career and reputation. The mere assertion that the results of an unspecified drug test were positive can completely undermine the respect and confidence of an employer or fellow employees, and subject the employee to sanctions, embarrassment, suspicion, and permanently taint their records. A positive drug test, even if the results were not due to the presence and detection of overt amounts of illicit or controlled substances, can result in termination and a continuing plague of problems.

The results of even the most modern drug tests may be affected by many harmless precursors, other prescription and non-prescription drugs. The tests themselves may also be attacked on a chain of custody theory in much the same manner as criminal evidence.

Employers, subject to the backlash of legal consequences for improper testing and the harms and damages which unfounded accusations could produce, have created a vested interest in employers and those performing routine drug testing to ensure the accuracy and reliability of those tests, and to similarly guarantee that the testing equipment will not be tampered with or questioned.

The public, particularly individuals who must submit to drug testing as a prerequisite for their employment and who are not drug users or abusers, have a vested interest in accurate testing and in ensuring that the testing methods are as free from possible intentional tampering or human error as they can be.

Law enforcement officials and investigators similarly want drug testing to be as accurate, reliable, and provable as possible so that the results will stand up in court or an administrative hearing. The public's interest in those cases where a positive drug test will lead to identifying an individual who has a chemical abuse problem, to ensure that person is prevented from jeopardizing the lives of others and receives the needed therapy and assistance, must also be considered.

Drug testing procedures currently in use generally require that a vial or specimen container be provided to the personnel supervising the testing, that the individual to be tested provide a sample of biological fluid, and that sample be forwarded to a laboratory facility for analytical testing.

While the currently employed methods vary depending upon the testing authority and the equipment provided, there are several common drawbacks to each method which have been identified.

Primarily, while the samples may sometimes be sealed in specimen containers once they have been obtained from the individual being tested, it cannot be verified that the equipment and containers being used for the testing were not tampered with, or were free of contaminants, prior to the testing. Similarly, the chain of custody prior to testing cannot be verified.

The testing equipment usually provides an ineffective seal for the specimen container, and only one seal when such is provided. The seal may frequently be neglected or omitted by the person supervising the testing. The person being tested often does not have an opportunity to inspect the testing equipment, an important factor to consider for purposes of belaying the apprehensions of the person being testing, or as a means of additional verification of the testing procedures. While a supervising person may be instructed in the proper testing and control procedures, there is always a chance of human error or the possibility that the supervisors will not understand the legal significance of the various steps of the process, and so the steps should be made as uniform, as often repeated, and as automatic as possible.

Tamper evident seals for plastic containers, such as those used in food packaging, are well known, a representative example being given by U.S. Pat. No. 4,087,018. Additional devices for securing a fluid container and evidencing tampering are known, such as those sealing closures disclosed in U.S. Pat. Nos. 1,996,682 and 4,262,814 and the related art. Another sealed container disposed within a second sealed package is disclosed in U.S. Pat. No. 985,850.

Each of these patents, while being representative of a broad field of art and disclosing a method of identifying or evidencing whether a container has been tampered with, each prove to have one or more defects making them unsuitable for application to the process of collecting a fluid biological sample for use as evidence.

Those containers in which an item or product is sealed so as to evidence tampering already contain the item to be protected. There is no provision for the container to exist in a tamper evidencing state prior to the product being placed therein, or for resealing the tamper evidencing closure once the item has been placed in the container. Similarly, there is no apparatus which automatically creates a new tamper evident seal when the container is closed once the original seal is broken, nor that enhances or facilitates verifying the chain of custody of the container. U.S. Pat. No. 4,362,698 discloses a permanently sealed laboratory vessel used in blood testing, however the manner of providing the closure to this vessel is unsuitable for use in the collection of biological samples in the field, or for preserving those samples during transportation to the testing facility.

BRIEF SUMMARY OF THE INVENTION

It is therefore one object of this invention to design an apparatus for collecting and preserving fluid biological samples for use in transporting those samples to a remote laboratory facility for analytical testing which eliminates many of the defects in the chain of custody associated with existing procedures, particularly the control of the sample collecting apparatus prior to the actual collection process.

It is another object of this invention to design the above apparatus such that it is highly tamper resistant along the entire chain of supply to the collection site, and transport to the testing facility.

It is a further object of this invention to design the above apparatus such that it promotes uniformity in testing, and encourages those supervising the drug testing to take the reasonable and necessary precautions to ensure the accuracy and reliability of such tests.

It is a still another object of this invention to design the above apparatus such that it includes uniform, repeated, and automated procedures for preserving the collection sample in a tamper resistant container.

It is a distinct object of this invention to design a method of collecting and preserving a fluid biological sample which utilizes the apparatus of this invention.

Briefly described, the apparatus for collecting and preserving fluid biological evidence of this invention comprises a specimen vial and lid, the lid having an adhesive coated disk inserted therein with the lid initially being inverted on the rim of the specimen vial, with the specimen vial and lid being encased in a tamper evident plastic wrapper. The specimen vial and lid, encased in the tamper evident wrapper, are sealed along with a pair of adhesive backed sealing tapes, an instruction manual, and a compressible foam cushioning pad, within an outer container having a correspondingly threaded lid.

Concisely, the method for using the above apparatus comprises the steps of breaking the tamper evident seal on the wrapper encasing the outer container and removing its contents, breaking the seal on the tamper evident wrapper which encases the specimen vial and lid, placing the fluid sample within the specimen vial, mounting the lid on the specimen vial such that the tamper evident adhesive coated disk within the lid contacts and seals the rim of the specimen vial, placing tamper evident adhesive coated tape across the lid of the specimen vial and down the opposing sides of the specimen vial, completing the chain of custody and placing it in the outer container along with the sealed specimen vial, replacing the foam pad, mounting the lid on the outer container, and placing tamper evident adhesive coated tape across the lid of the outer container and down the opposing sides of the outer container.

DESCRIPTION OF THE PREFERRED EMBODIMENTS

The apparatus for collecting and preserving fluid biological evidence of this invention is shown in FIGS. 1–4 and referenced generally therein by the numeral 10.

Figure 1:
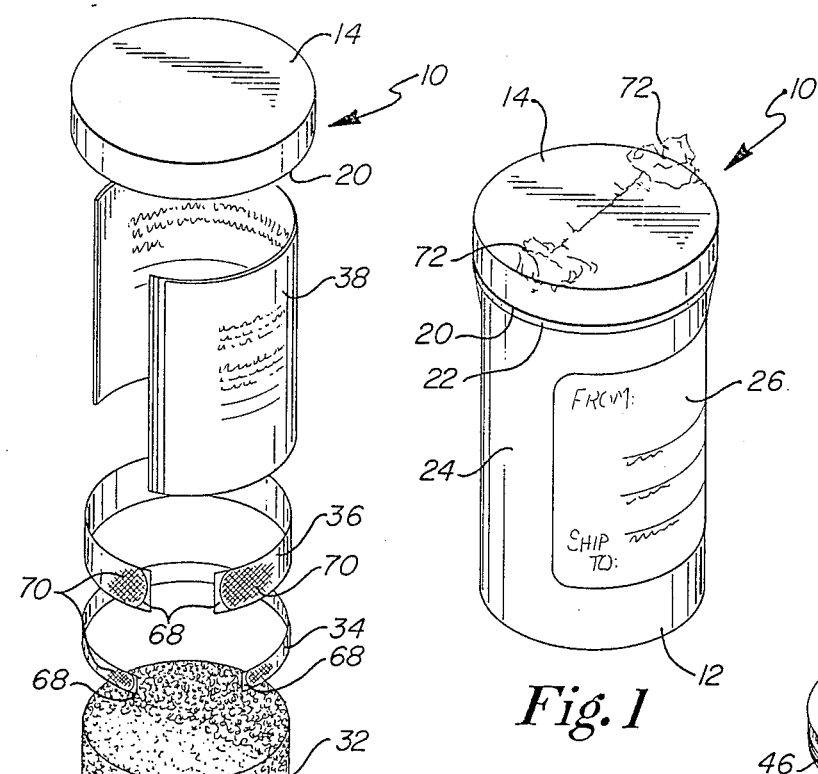
FIG. 1 is a perspective view of the outside container of the apparatus for collecting and preserving fluid biological evidence of this invention.

Referring to FIG. 1, it may be seen that the apparatus 10 is contained within an outer mailing container having a generally cylindrical, plastic outer container body 12 with a lid 14 having inner threads (not shown) aligned to engagingly mesh or seal with threads 16 along or below the rim 18 of the container body 12. The lower edge 20 of the lid 14 also abuts against the upper surface of a sealing collar 22 which projects approximately perpendicularly from the outer wall surface 24 of the outer container body 12. An adhesive mailing or routing label 26 is attached to the outer wall surface 24 of the outer container body 12 having pertinent information such as the mailing address of an analytical testing laboratory or other predetermined destination preprinted thereon, or having the necessary space available for such information to be added. The outer container 12 and lid 14 should be molded from a resilient, impact resistant, opaque plastic resin.

Figure 2:
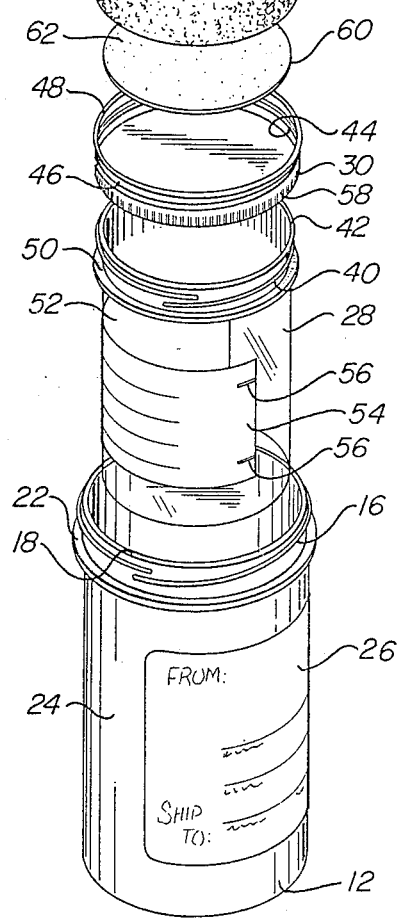
FIG. 2 is an exploded view of the collection apparatus of FIG. 1.

Referring to FIG. 2, it may be seen that slidably received within the outer container 12 are an inner container 28 and corresponding lid 30, a foam cushioning pad 32, a pair of sealing tapes 34, 36, and an instruction booklet 38.

The inner container or specimen vial 28 is manufactured from a uniform mixture of polystyrene and K-resin, having a generally cylindrical shape and a capacity of approximately 90–100 cc. The specimen vial 28 should be substantially transparent or translucent, or should have a clear window portion extending the height of the specimen vial 28, such that the level or quantity of any fluid content can be readily and visibly observed.

The top portion of the specimen vial 28 has a threaded region 40 adjacent the top rim 42 which are sized and aligned to sealing engage threads 44 along the inside of the skirt portion 46 of the lid 30. The lower edge 48 of the skirt 46 of the lid 30 is similarly designed to sealingly contact a sealing collar 50 projecting from the body surface 52 of the specimen container 28 below the threaded region 40.

An adhesive backed specimen identification label 54 is attached to the outer body surface 52 of the specimen vial 28, the specimen identifying label 54 having the appropriate preprinted information identifying the source of the specimen vial 28, and suitable space available for identifying the individual or entity supplying the fluid evidence contained therein. The specimen vial should also contain a pair of indicators 56 which specify the minimum and maximum specimen quantity which is necessary for testing, and which ensures the safe transportation of the specimen vial 28. In the case of a transparent or translucent specimen vial 28, the indicators 56 may comprise preprinted lines on the specimen label 54 positioned and aligned to correspond to the minimum and maximum levels associated with the particular dimensions of the container. In the case of human urine specimens, the upper and lower limit indicators 56 should designate approximately 65 cc. and 25 cc. respectively.

The lid 30 for the specimen vial 28 has a knurled or serrated peripheral edge 58 which aids in securing the lid 30 onto the threaded portion 40 of the vial 28 to form an engaging and fluid-tight seal. A styrene foam sealing disk 60 is inserted into the lid 30 for the specimen vial 28, the disk 60 having an adhesive coated surface 62, and a non-adhesive coated, opposite surface 64 having generally linear printed lines or text 66 extending across it.

Initially, the specimen vial 28, lid 30, and foam sealing disk 60 are sealed together within a generally brittle, tamper resistent wrapper (not shown) made from a clear plastic thermal shrink-wrap material. The lid 30 is initially inverted on the vial 28, with the foam sealing disk 60 inserted within the lid 30 such that the lower edge 48 of the lid 30 and adhesive surface 62 of the sealing disk 60 are facing upwards, away from the specimen vial 28.

The foam cushioning pad 32 should be constructed of a compressible synthetic foam rubber or plastic sponge material, having a generally cylindrical shape slightly greater than or equal in diameter to the inner diameter of the outer container 12, and should have a height slightly greater than the distance between the lid 30 of the specimen vial 28 and the inner surface of the lid 14 of the outer container 12 when the lid 30 is sealed on the specimen vial 28.

The pair of sealing tapes 34, 36 each have an adhesive backing and are affixed to a non-adhering backing strip 68 from which they may be removed by peeling the length of the tapes 34, 36 the lengths of the strips 68. One tape 34 has a shorter length and narrower width sufficient to extend diagonally across the lid 30 of the specimen vial 28 and downwardly on both sides of the specimen vial 28 across the sealing collar 50, and a substantial distance downward along the outer surface 52 of the specimen vial 28. One tape 36 has a greater width and a greater length sufficient to extend diagonally across the lid 14 of the outer container 12 and downwardly on both sides of the container 12 across the sealing collar 22, and a substantial distance downward along the outer surface 24 of the container 12. Each sealing tape 34, 36 is preferable constructed from a 32# paper with an adhesive coating which will not permit the tapes 34, 36 to be removed without visibly tearing or delaminating, and each tape 34, 36 should similarly have a printed safety pattern 70. The sealing tapes 34, 36 should extend along the opposing sides of the respective vial 28 or outer container 12 a substantial distance such that said sealing tapes 34, 36 cannot be removed without evidencing that removal.

The instruction manual 38 may be in leaflet or booklet form, with instructions for obtaining and preserving the evidence sample, handling the apparatus 10 for transportation, and recording the chain of custody printed thereon. The instruction manual 38 should also contain a document upon which each intervening step in the collection and testing procedure may be recorded by the person undertaking that step of the procedure, so as to evidence and verify the chain of custody of the specimen vial 28.

The instruction manual 38 should be thin and flexible such that it may be curled around the specimen vial 28 and lid 30, and inserted between the specimen vial 28 and lid 30 and the outer container 12. The shrink-wrap encased specimen vial 28 and lid 30 must similarly be sized so as to be slidably received within the outer container 12 with the instruction manual 38 and sealing tapes 34, 36 disposed between the vial 28 and lid 30 and the outer container 12. The sealing tape 34 for the specimen vial 28 may also be folded and sealed within the protective tamper-resistant wrapper surrounding the specimen vial 28 and lid 30.

The specimen vial 28, lid 30, and foam disk 60 sealed within the protective tamper-resistant wrapper are inserted into the outer container 12, with the sealing tapes 34, 36 and instruction manual 38 wrapper thereabout. The foam cushioning pad 32 is inserted into the outer container 12 on top of the specimen vial 28 and lid, and is compressed therebetween as the lid 14 is securely attached to the outer container 12. The entire outer container 12 enclosing the apparatus 10 is then sealed within a tamper resistent outer wrapper 72 (FIG. 1) similarly made from a clear plastic thermal shrink-wrap material.

In operation, a person initially obtaining a specimen of biological fluid to be used as evidence will break the seal on and unwrap the apparatus 10 from the tamper resistant outer wrapper 72 which surrounds the outer container 12 and lid 14. The lid 14 is detached from the outer container 12, and the foam cushioning pad 32, and sealed specimen vial 28 and lid 30 are removed from the outer container 12. Similarly, the instruction manual 38 and sealing tape 36 are then removed from the outer container 12.

Following the instructions provided on the instruction manual 38, the person removes the lid 30, seal 34 and specimen vial 28 from the protective tamper-resistant wrapper. The biological fluid specimen is then placed directly into the specimen vial 28 up to a level between the indicators 56 showing a sufficient but not excessive quantity of fluid. The lid 30 is then inverted and engaged on the rim 42 of the specimen vial 28, being rotated corresponding to the direction of the threads 40, 42 in order to bring the adhesive surface 62 of the foam disk 60 into contact with the rim 42 so as to sealingly engage therewith around the periphery of the rim 42. The lid 30 should therefore be securely fastened to the specimen vial 28 such that the lower edge 48 of the skirt 46 closely confronts or engages the collar 50.

Figure 3:
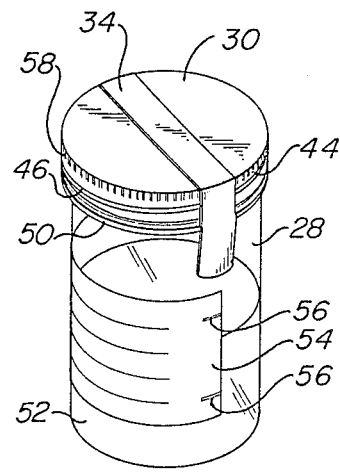
FIG. 3 is a perspective view of the filled inner container of the apparatus of FIG. 1 with the protective seals intact.

The shorter sealing tape 34 is then peeled from the corresponding backing strip 68 and applied to the lid 30 and side surfaces 52 of the specimen vial 28. The sealing tape 34 is firmly pressed into sealing contact with the lid 30 and vial 28 along the entire length of the sealing tape 34, as shown in FIG. 3.

Any necessary information concerning the individual supplying or the person collecting the fluid sample is then recorded on the specimen label 54, and the specimen vial 28 and lid 30 are slidingly inserted into the outer container 12. The intervening steps are recorded on the document contained in the instruction manual 38 for verifying the chain of custody, and this document is similarly placed in the outer container 12. The foam cushioning pad 32 is then inserted on top of the lid 30 of the specimen vial 28, and the lid 14 of the outer container 12 is engaged on the rim 18 of the outer container 12, being rotated thereon corresponding to the direction of the threads 16 in order to bring the lower edge 20 of the lid 14 into close confronting contact with the collar 22 of the outer container 12 to form a sealing contact therebetween.

The longer sealing tape 36 is then peeled away from the corresponding backing strip 68 and applied to the lid 14 and outer container 12 in a manner similarly described above in relation to sealing the specimen vial 28 and lid 30. Any additional pertinent information may be recorded on the mailing or routing label 26, and the apparatus 10 may then be delivered to the appropriate laboratory or analytical testing facility.

Figure 4:
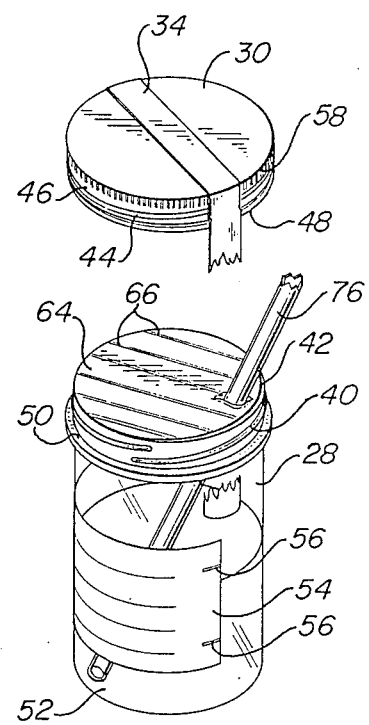
FIG. 4 is a perspective view of the inner container of the apparatus of FIG. 1 with the seals opened and the fluid being removed by a pipette.

Referring to FIG. 4, it may be seen that a technician or other laboratory personnel who will perform the necessary testing or analysis on the fluid evidence breaks the sealing tape 36 on the outer container 12 and lid 14, and removes the foam cushioning pad 32, and sealed specimen vial 28 and lid 30. The technician then records the intervening steps on the document contained in the instruction manual 38 which verifies the chain of custody of the specimen vial 28. The technician then breaks the sealing tape 34 on the specimen vial 28 and lid 30, and completely unscrews the lid 30 from the specimen vial 28. The technician then removes all or a portion of the foam sealing disk 60 from the rim 42 of the specimen vial 28 by peeling it therefrom, or punctures the disk 60 with an appropriate instrument. The technician then removes aliquots of the fluid sample using a pipette 76 or other suitable instrument. The technician may then perform the necessary analysis on the aliquots of fluid removed from the specimen vial 28.

In a varying embodiment of the apparatus for collecting and preserving fluid biological evidence 10 described above, a 1000 mg. portion of granular sodium fluoride, or other suitable chemical agent which will not interfere with the analytical testing, may initially be placed within the specimen vial 28 and which will function to preserve the fluid sample until such time that the specimen vial 28 is unsealed and opened for removal of the contents.

While the preferred embodiments of the particular invention have been described above in relation to the referenced drawing Figures, it is understood that the apparatus and method of using the apparatus described above may be modified and changed without departing from the spirit and scope of the appended claims.

What is claimed is:

1. An apparatus for collecting and preserving a sample of a biological fluid for evidentiary purposes, said apparatus comprising:
    a vial, said vial defining a first aperture and a first receptacle region for containing a sample;
    a first lid, said first lid being engagingly mountable on said vial adjacent said first aperture to form a removable closure over said first aperture;
    sealing means for producing a removable fluid tight seal between said vial and said first lid when said first lid is engagingly mounted on said vial;
    a tamper evident wrapper means, said wrapper means initially encasing said vial, said first lid, and said sealing means with said first lid being inverted upon said vial such that said sealing means does not form said fluid tight seal between said vial and said first lid,
    an outer container for initially receiving said vial and said first lid, said outer container defining a second aperture through which said vial and said lid and said sealing means encased in said tamper evident wrapper means may be inserted, and a second receptacle region which may receive and contain said vial, said lid, said sealing means, and said tamper evident wrapper means; and
    a second lid, said second lid being engagingly mountable on said outer container adjacent said second aperture to form a removable closure over said second aperture, whereby a person collecting the sample may remove the vial, the first lid, and the sealing means from the tamper evident wrapper means, place the sample within the first receptacle of the vial, engagingly mount the first lid on the vial such that the sealing means forms the fluid tight seal therebetween, and then return the vial and lid to the second receptacle region within the outer container.

2. The apparatus of claim 1 wherein the vial has a peripheral rim adjacent to and surrounding the first aperture, said sealing means comprises:
    a disk, said disk being insertable within the first lid, said disk having a peripheral edge substantially conforming to the peripheral rim of the vial, said disk having a surface coated with an adhesive, said adhesive extending across said surface of said disk at least around a portion of said disk adjacent to said peripheral edge of said disk, whereby said adhesive forms a fluid tight seal between said disk and the rim of the vial when the surface of the disk coated with the adhesive is pressed into contact with the rim of the vial.

3. The apparatus of claim 2 wherein the rim is generally circular and the disk is generally circular, the disk and the rim each have a diameter, said diameter of the disk being slightly greater than or substantially equal to said diameter of the rim.

4. The apparatus of claim 2 wherein the adhesive coating covers substantially the entire surface of the disk.

5. The apparatus of claim 1 further comprising:
    a first tamper evident sealing tape, said first tamper evident sealing tape having an adhesive backing and a length and two ends, said length being sufficient such that said first tamper evident sealing tape may be attached to the vial and the first lid so as to extend across the first lid and extending substantially downward to contact and adhere to the vial.

6. The apparatus of claim 1 wherein the fluid sample is to comprise a volume within a predetermined range of acceptable volumes between a minimum volume and a maximum volume, at least a portion of the vial being sufficiently translucent to permit visual observation of the same contained therein, said apparatus further comprising:
    indicator means associated with said vial for identifying by visual comparison the volume of the fluid sample relative to the minimum volume and the maximum volume, whereby a viewer may determine by visual inspection whether the volume of the fluid sample is within the predetermined range of acceptable volumes.

7. The apparatus of claim 6 wherein the vial has a substantially translucent or transparent portion, and said indicator means comprises:

a label attached to the vial, said label having a marking adjacent the translucent or transparent portion corresponding to the maximum volume, said label further having a marking adjacent the translucent or transparent portion corresponding to the minimum volume.

8. The apparatus of claim 1 wherein the outer container and second lid are substantially enclosed within a second tamper evident wrapper means.

9. The apparatus of claim 1 further comprising a cushioning pad, said cushioning pad being positioned between the vial and the outer container so as to prevent the vial from contacting the outer container.

10. The apparatus of claim 1 wherein the outer container has a generally cylindrical shape.

11. The apparatus of claim 1 wherein the outer container further has a routing label attached thereto.

12. The apparatus of claim 1 wherein the vial contains an aliquot of granular sodium fluoride.

13. The apparatus of claim 12 wherein the aliquot of sodium fluoride has a weight of approximately one gram.

14. The apparatus of claim 1 wherein the outer container has a pair of opposing sides adjacent the second lid when the second lid is mounted upon the outer container, said apparatus further comprising:
a tamper evident sealing tape having a length and two ends and an adhesive backing, said length being sufficient such that said tamper evident sealing tape may be secured by means of said adhesive backing over said second lid with each of said two ends of said sealing tape extending downwardly over one of the opposing sides of the outer container.

15. A method for collecting and preserving a fluid biological sample for evidentiary purposes, said method comprising the steps of:
breaking a seal of a tamper evident closure which encases a vial having a receptacle region and an aperture and a rim surrounding said aperture, a lid which may be engagingly mounted on said rim, and an adhesive sealing means contained within said lid and initially separated from said vial by said lid;
removing said tamper evident closure from said vial and said lid;
placing the fluid sample through said aperture and within said receptacle region of said vial; and
engagingly mounting said lid on the vial such that said adhesive sealing means contacts said rim of said vial and forms a fluid tight seal therewith.

16. The method of claim 15 further comprising the step of:
placing a tamper evident sealing tape having an adhesive backing across said lid and downward substantially along said vial with said adhesive backing contacting and adhering to said lid and said vial such that said tamper evident sealing tape will show visible signs of tampering if said lid is removed from said vial.

17. The method of claim 15 further comprising the steps of:
breaking a seal of a tamper evident closure which encases an outer container and second lid, said outer container defining a second aperture and a second receptacle region, said second lid being engagingly mounted on said outer container creating a closure over said second aperture, said outer container enclosing the vial, the lid, the adhesive sealing means, and the tamper evident wrapper;
removing the second lid from the outer container; and removing the vial, the lid, and the adhesive sealing means from said outer container through said second aperture.

18. The method of claim 17 wherein the outer container has a pair of opposing sides, said method further comprising the steps of:
returning the vial with the fluid sample contained therein and the lid mounted thereon through the second aperture to within the second receptacle region; and
placing a tamper evident sealing tape having an adhesive backing across said second lid and downwardly substantially along the outer container with said adhesive backing contacting and adhering to said second lid and the outer container such that said tamper evident sealing tape will show visible signs of tampering if said second lid is removed from said outer container.

19. The method of claim 17 further comprising the step of:
placing a document recording a chain of custody for the vial within the outer container.

20. The method of claim 15 wherein the fluid sample has a volume within a predetermined range of acceptable volumes between a minimum volume and a maximum volume, at least a portion of the vial being sufficiently translucent to permit visual observation of the sample contained therein, said method further comprising the step of:
identifying by visual comparison the volume of the fluid sample within the vial relative to an indicator means on said vial corresponding to the minimum volume and the maximum volume, whereby the visual comparison discloses whether the volume of the fluid sample is within the predetermined ranger of acceptable volumes.

* * * * *